United States Patent [19]

Eric et al.

[11] 4,062,889

[45] Dec. 13, 1977

[54] PREPARATION OF SULFONYLUREAS

[76] Inventors: Lucien Eric, 1141 Lucerne Road, Mount Royal, Montreal 305; Francis L. Chubb, 4835 Pierre Lauzon, Pierre Fondes 910, both of Canada

[21] Appl. No.: 144,271

[22] Filed: May 17, 1971

[30] Foreign Application Priority Data

May 21, 1970 Canada .................................. 083550

[51] Int. Cl.$^2$ .......................................... C07C 127/19
[52] U.S. Cl. ................................ 260/553 D; 560/166
[58] Field of Search ........................ 260/553 D, 482 C

[56] References Cited

U.S. PATENT DOCUMENTS

| 3,013,072 | 12/1961 | McLamore et al. | 260/553 D |
| 3,108,098 | 11/1963 | McManus | 260/553 D X |

FOREIGN PATENT DOCUMENTS

| 476,305 | 12/1952 | Italy | 260/482 C |
| 935,980 | 9/1963 | United Kingdom | 260/553 D |

*Primary Examiner*—James O. Thomas, Jr.
*Assistant Examiner*—G. T. Britenstein
*Attorney, Agent, or Firm*—Kevin B. Clarke

[57] ABSTRACT

Sulfonylureas are prepared by reacting a hydroxyethyl carbamate with an alkali metal salt of a substituted benzene sulfonamide, the alkali metal being selected from the group comprising sodium, potassium and lithium.

8 Claims, No Drawings

PREPARATION OF SULFONYLUREAS

This invention relates to the production of sulfonylureas having well known beneficial pharmacological properties.

The present invention provides sulfonylureas of the general formula:

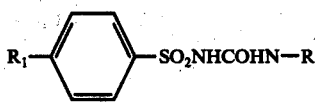

wherein R is either a propyl, butyl or cyclohexyl radical and $R_1$ is selected from the group of radicals comprising hydrogen, a lower alkyl having one to four straight or branched carbon atoms, a halogen, and an unsubstituted or a mono or disubstituted benzamido alkylene having one to four straight or branched carbon atoms.

The present invention relates to the preparation of sulfonylureas of the above general formula by reacting with a hydroxyethyl carbamate an alkali metal salt of a substituted benzene sulfonamide, the alkali metal being selected from the group comprising sodium, potassium and lithium.

The reactant hydroxyethyl carbamate may be prepared by reacting an amine of the general formula $RNH_2$, in which R has the same definition of radicals as given above, with an alkylene carbonate after which the separated and purified hydroxyethyl carbamate is reacted with the selected alkali metal salt of a substituted benzene sulfonamide. However, it has been found that good yields are obtained if the alkali metal salt of a substituted benzene sulfonamide is reacted with the reactant hydroxyethyl carbamate preformed in situ.

The invention will now be illustrated by the following examples of the preparation of specific and well known sulfonylureas having proven beneficial pharmacological properties.

EXAMPLE 1

1-[p-(2-{5-chloro-2-methoxybenzamido}ethyl)-benzenesulfonyl]-3-cyclohexyl urea a. A mixture of cyclohexylamine (2.98 g.) and ethylene carbonate (2.64 g.) was heated at 40°–50° for 20 hours. p-(2-{5-chloro-2-methoxybenzamido}ethyl)-benzene sulfonamide (5.87 g. as sodium salt) and DMF (50 ml.) were added and the mixture heated at 110° for 3 hours. The solvent was evaporated in vacuo and the residue was treated with water (120 ml.). Unreacted sulfonamide (1.8 g.) thereby precipitated was filtered off. Crude 1-[p-(2-{5-chloro-2-methoxybenzamido}ethyl)-benzensulfonyl]-3-cyclohexyl urea was obtained from the acidified filtrate and crystallized twice from methanol to give the required sulfonylurea, m.p. 166°–9° (i-r identical with authentic sample).

b. A mixture of p-(2-{5-chloro-2-methoxybenzamido}ethyl)-benzene sulfonamide (2.78 g. as sodium salt) and hydroxyethylcyclohexyl carbamate (2.67 g.) in DMF (40 ml.) was heated at 110° for 4 hours. The solvent was evaporated in vacuo and the residue was treated with hot water (75 ml.). The solid was filtered off, and the filtrate acidified to congo red. The gummy precipitate was separated and crystallized twice from methanol to give the required sulfonylurea, m.p. 166°–9° (i-r identical with authentic sample).

EXAMPLE 2

1-(4-chloro-benzenesulfonyl)-3-n-propyl-urea.

a. A mixture of ethylene carbonate (8.14 g.) and n-propylamine (5.46 g.) was stirred at 40° for 20 hours. To this solution was added p-chlorobenzenesulfonamide (9.35 g. as sodium salt) and DMF (100 ml.), and the resulting mixture was heated at 110° for 3 hours. The solvent was removed in vacuo and the residue was dissolved in hot water (50 ml.). The solution was cooled and the pH adjusted to 8 with 10% aqueous acetic acid. The unreacted sulfonamide thus precipitated was filtered, and the filtrate was acidified to precipitate the crude 1-(4-chloro-benzenesulfonyl)-3-n-propyl-urea. This was purified by crystallization from aqueous ethanol to give a sample m.p. 123°–126° (i-r identical with an authentic sample).

b. Hydroxyethyl n-propyl carbamate (9.8 g.) and p-chlorobenzene sulfonamide (6.7 g. as sodium salt) in DMF (175 ml.) was heated at 110° for 3 hours. The product was filtered and the solvent evaporated in vacuo to give an oily residue. This residue was dissolved in water (100 ml.) and the solution adjusted to pH 8. A precipitate of unreacted sulfonamide (1.9 g., 28%) was filtered off, and the filtrate adjusted to pH 5 with 10% aqueous acetic acid to yield crude 1-(4-chloro-benzene-sulfonyl)-3-n-propyl-urea (3.2 g., 46%). Recrystallization from ethanol-water gave a sample m.p. 123°–126° (i-r identical with an authentic sample).

c. n-Propylamine (5.9 g., 0.1 mole.) and propylene carbonate (10.2 g., 0.1 mole.) were mixed and heated at 60° over night. To the resulting hydroxypropyl-n-propylcarbomate were added p-chlorobenzene sulfonamide (10.67 g., as sodium salt) and DMF (200 ml.) and the mixture was heated at 120° for 4 hours. After evaporation of the solvent the residue was taken up in water (200 ml.) and the solution adjusted to pH 8 by the addition of acetic acid. Unreacted p-chlorobenzene sulfonamide (2 g.) separated out and was collected. Further adjustment to pH 5 precipitated 1-(4-chloro-benzenesulfonyl)-3-n-propyl-urea (2 g.) whose infrared spectrum was identical with that of an authentic sample.

EXAMPLE 3

1-(p-toluenesulfonyl)-3-n-butyl-urea.

a. A mixture of ethylene carbonate (8.14 g.) and n-butylamine (6.79 g.) was stirred at 40° for 20 hours. To this solution was added p-toluenesulfonamide (8.92 g. as sodium salt) and DMF (125 ml.). After stirring for 3 hours at 120°–130° the solution was cooled and filtered. The filtrate was evaporated in vacuo and the residue was treated with water (100 ml.). Insoluble material was filtered off and the filtrate acidified. The crude 1-(p-toluenesulfonyl)-3-n-butyl-urea thus precipitated was collected and purified by crystallization from alcohol to give a sample m.p. 125°–127° (i-r identical with authentic sample).

b. Hydroxyethyl n-butyl carbamate (6.84 g.) and p-toluenesulfonamide (4.10 g. as sodium salt) in DMF (175 ml.) were heated at 110° for 3 hours. The product was filtered, the solvent evaporated in vacuo, and the residue taken up in water (100 ml.). A small insoluble residue of unreacted sulfonamide (500 mg., 7.3%) remained. The pH of the solution was adjusted to 8 with 10% aqueous acetic acid and the resulting precipitate was filtered off. The filtrate was acidified with 10% aqueous acetic acid to yield crude 1-(p-toluenesulfonyl)-

3-n-butyl-urea (1.8 g., 18%). One recrystallization gave a sample m.p. 126°–128° (i-r identical with authentic sample).

c. n-Butylamine (7.3., 0.1 mole.) and propylene carbonate (10.2 g., 0.1 mole.) were mixed and warmed at 60° for 24 hours. To the resulting hydroxypropyl-n-butyl carbamate were added p-toluene sulfonamide (10 g. as sodium salt) and DMF (200 ml.) and the mixture heated at 120° for 4 hours. The solvent was evaporated under reduced pressure, water (200 ml.) added to the oily residue, and the mixture heated for 10 minutes on the steam bath. Upon cooling unreacted p-toluenesulfonamide (1.7 g.) separated out and was collected. The filtrate was acidified with dilute aqueous acetic acid and the crude 1(p-toluenesulfonyl)-3-n-butyl-urea (4.0 g., 40%) collected. An infrared spectrum of a recrystallized sample was identical with that of an authentic sample.

From the examples it will be observed that the process can be conducted either by forming the hydroxyethyl carbamate with subsequent separation and then reacting it with the particular metal salt or else the process may be conducted in one stage by reacting together the preformed hydroxyethyl carbamate in situ.

What is claimed is:

1. A process or preparing a sulfonylurea selected from the group consisting of 1-[p-(2-{5-chloro-2-methoxybenzamido}ethyl)benzenesulfonyl]-3-cyclohexyl urea; 1-(4-chlorobenzene-sulfonyl)-3-n-propyl urea and 1-(p-toluenesulfonyl-3-n-butyl urea which comprises reacting a sodium, potassium or lithium salt of an appropriate substituted benzene sulfonamide with an hydroxyethyl carbamate at temperatures of from 110° to 130° C in the presence of dimethylformamide solvent and recovering the desired product from the reaction medium.

2. A process according to claim 1 wherein the hydroxethyl carbamate is prepared by reacting an amine of the general formula $RNH_2$ wherein R is a propyl, butyl or cyclohexyl radical with an alkylene carbonate at temperatures ranging from 40° to 60° C.

3. A process according to claim 1 wherein 1-[p-(2-{5-chloro-2-methoxybenzamido}ethyl) benzenesulfonyl]-3-cyclohexyl-urea is prepared by reacting p-(2-{5-chloro-2-methoxybenzamido}ethyl)-benzene sulfonamide sodium salt with hydroxyethyl cyclohexyl carbamate.

4. The process according to claim 3 wherein the hydroxyethyl cyclohexyl carbamate is prepared by reacting cyclohexyl amine and ethylene carbonate at temperatures ranging from 40° to 50° C and then treated in situ with the sodium salt.

5. A process according to claim 1 wherein 1-(4-chlorobenzenesulfonyl)-3-n-propyl urea is prepared by reacting p-chlorobenzenesulfonamide sodium salt with hydroxyethyl n-propyl carbamate.

6. The process according to claim 5 wherein the hydroxyethyl-n-propyl carbamate is prepared by reacting n-propylamine and ethylene carbonate at 40° C and then treated in situ with the sodium salt.

7. A process according to claim 1 wherein 1-(p-toluenesulfonyl-3-n-butyl-urea is prepared by reacting p-toluenesulfonamide sodium salt with hydroxyethyl-n-butyl carbamate.

8. The process according to claim 7 wherein the hydroxyethyl-n-butyl carbamate is obtained by reacting n-butylamine and ethylene carbonate at 40° C and then treated in situ with the sodium salt.

* * * * *